United States Patent
Naik et al.

(10) Patent No.: US 11,508,481 B2
(45) Date of Patent: Nov. 22, 2022

(54) MACHINE-LEARNED HORMONE STATUS PREDICTION FROM IMAGE ANALYSIS

(71) Applicant: salesforce.com, inc., San Francisco, CA (US)

(72) Inventors: Nikhil Naik, Palo Alto, CA (US); Ali Madani, Palo Alto, CA (US); Nitish Shirish Keskar, San Francisco, CA (US)

(73) Assignee: Salesforce, Inc., San Francisco, CA (US)

( * ) Notice: Subject to any disclaimer, the term of this patent is extended or adjusted under 35 U.S.C. 154(b) by 263 days.

(21) Appl. No.: 16/895,983

(22) Filed: Jun. 8, 2020

(65) Prior Publication Data

US 2021/0280311 A1   Sep. 9, 2021

Related U.S. Application Data

(60) Provisional application No. 62/986,479, filed on Mar. 6, 2020.

(51) Int. Cl.
*G16H 50/20* (2018.01)
*G06K 9/62* (2022.01)
(Continued)

(52) U.S. Cl.
CPC ........... *G16H 50/20* (2018.01); *G06K 9/6257* (2013.01); *G06K 9/6262* (2013.01); *G06N 5/04* (2013.01);
(Continued)

(58) Field of Classification Search
CPC ........ G16H 50/20; G16H 10/20; G16H 10/40; G16H 30/40; G06K 9/6257; G06K 9/6262;
(Continued)

(56) References Cited

U.S. PATENT DOCUMENTS

2019/0347557 A1\* 11/2019 Khan .................... G06N 3/0454
2020/0388028 A1\* 12/2020 Agus ..................... G06T 7/0012
(Continued)

OTHER PUBLICATIONS

Gurcan, "Computerized pathological image analysis for neuroblastoma prognosis", 2007 (Year: 2007).\*
(Continued)

*Primary Examiner* — Juan A Torres
(74) *Attorney, Agent, or Firm* — Fenwick & West LLP

(57) ABSTRACT

An analytics system uses one or more machine-learned models to predict a hormone receptor status from a H&E stain image. The system partitions H&E stain images each into a plurality of image tiles. Bags of tiles are created through sampling of the image tiles. The analytics system trains one or more machine-learned models with training H&E stain images having a positive or negative receptor status. The analytics system generates, via a tile featurization model, a tile feature vector for each image tile a test bag for a test H&E stain image. The analytics system generates, via an attention model, an aggregate feature vector for the test bag by aggregating the tile feature vectors of the test bag, wherein an attention weight is determined for each tile feature vector. The analytics system predicts a hormone receptor status by applying a prediction model to the aggregate feature vector for the test bag.

20 Claims, 7 Drawing Sheets

(51) Int. Cl.
*G06N 5/04* (2006.01)
*G16H 10/20* (2018.01)
*G06N 20/00* (2019.01)

(52) U.S. Cl.
CPC .............. *G06N 20/00* (2019.01); *G16H 10/20* (2018.01); *G06V 2201/03* (2022.01)

(58) Field of Classification Search
CPC ...... G06N 5/04; G06N 20/00; G06V 2201/03; G06V 20/69; G06T 2207/10056; G06T 2207/20081; G06T 2207/20084; G06T 2207/30024; G06T 2207/30068; G06T 7/0012
USPC ......................................................... 382/133
See application file for complete search history.

(56) References Cited

U.S. PATENT DOCUMENTS

2021/0216746 A1* 7/2021 Nie ...................... G06V 20/698
2021/0350176 A1* 11/2021 Klaiman ............... G06F 3/0482

OTHER PUBLICATIONS

Campanella, G. et al., "Clinical-grade computational pathology using weakly supervised deep learning on whole slide images," Nature Medicine 25(8), Aug. 2019, pp. 1-21.

Couture, H.D. et al., "Image analysis with deep learning to predict breast cancer grade, ER status, histologic subtype, and intrinsic subtype," Nature Partner Journals Breast Cancer 4(30), Sep. 3, 2018, pp. 1-8.

Devries, T. et al., "Improved Regularization of Convolutional Neural Networks with Cutout," arXiv: 1708.04552v2, Nov. 29, 2017, pp. 1-8.

Ilse, M. et al., "Attention-based Deep Multiple Instance Learning," arXiv: 1802.04712v4, Jun. 28, 2018, pp. 1-16.

Otsu, N., "A Threshold Selection Method from Gray-Level Histograms," IEEE Transactions on Systems, Man and Cybernetics, vol. SMC-9, No. 1, Jan. 1979, pp. 62-66.

Nikhil, N. et al., "Deep learning-enabled breast cancer hormonal receptor status determination from base-level H&E stains," Nature Communications, vol. 11, No. 1, Nov. 16, 2020, pp. 1-8.

PCT International Search Report and Written Opinion, PCT Application No. PCT/US2020/066501, dated Mar. 12, 2021, 17 pages.

Qaiser, T. et al., "Learning Where to See: A Novel Attention Model for Automated Immunohistochemical Scoring," IEEE, Mar. 26, 2019, pp. 1-14.

Shrivasrava, A. et al., "Training Region-Based Object Detectors with Online Hard Example Mining," 2016 IEEE Conference on Computer Vision and Pattern Recognition, Jun. 1, 2016, pp. 761-769.

* cited by examiner

300

Access a first set of H&E stain images of tissue samples with positive hormone receptor status and a second set of H&E stain images of tissue samples with negative hormone receptor status
310

For each H&E stain image, partition the H&E stain image into a plurality of image tiles
320

For each H&E stain image, sample a subset of image tiles
330

Train a featurization model configured to generate a tile feature vector for an image tile
340

Train an attention model configured to generate an aggregate feature vector for a H&E stain image by aggregating the tile feature vectors of the image tiles in the sampled subset
350

Train a prediction model configured to predict hormone receptor status using the aggregate feature vector from a H&E stain image
360

FIG. 3

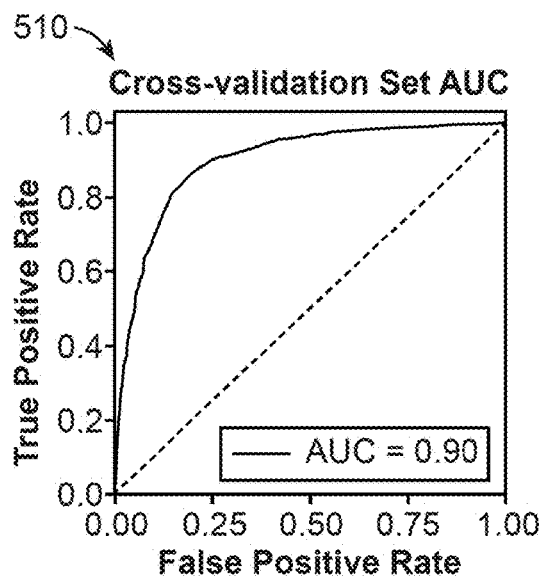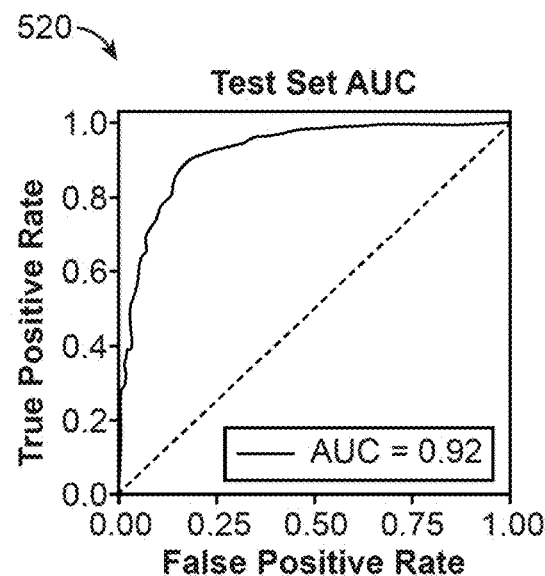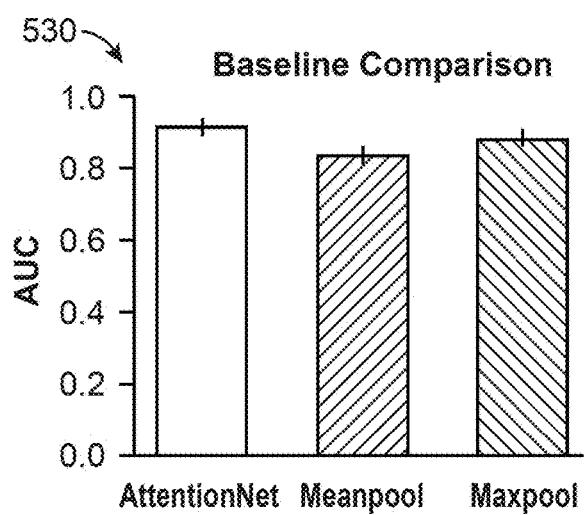
FIG. 5

MACHINE-LEARNED HORMONE STATUS PREDICTION FROM IMAGE ANALYSIS

CROSS REFERENCE TO RELATED APPLICATIONS

This application claims the benefit of U.S. Provisional Application No. 62/986,479, filed Mar. 6, 2020, which is hereby incorporated in its entirety by reference.

BACKGROUND

This present disclosure generally relates to the use of machine-learned models for the prediction of hormone receptor status (e.g., estrogen receptor status or ERS) from haematoxylin and eosin (H&E) stain images.

For newly diagnosed breast cancer, ERS is a key molecular marker used for prognosis and treatment decisions. During clinical management, ERS is determined by pathologists from immunohistochemistry (IHC) staining of biopsied tissue for the target receptor. IHC staining is generally an expensive and time-consuming process as a pathologist trained in IHC staining and evaluation is needed to determine the ERS. However, relying on human pathologists can lead to discordance in results due to variability in IHC preparation and pathologist subjectivity.

A method for predicting hormone receptor status using machine-learned models comprises accessing a test haematoxylin and eosin (H&E) stain image of a test tissue sample; partitioning the test H&E stain image into a plurality of image tiles; sampling a subset of image tiles from the plurality of image tiles for the test H&E stain image; generating a tile feature vector for each image tile of the sampled subset of image tiles; generating an aggregate feature vector for the test H&E stain image by aggregating the tile feature vectors of the image tiles in the sampled subset; and predicting a hormone receptor status by applying a prediction model to the aggregate feature vector for the test H&E stain image, wherein the prediction model is trained with a first set of H&E stain images from a first set of tissue samples having a positive hormone receptor status and a second set of H&E stain images from a second set of tissue samples having a negative hormone receptor status. In additional embodiments, a non-transitory computer-readable storage medium stores instructions for performing the methods described herein. In additional embodiments, a system configured to perform the methods described herein comprises a processor and the non-transitory computer-readable storage medium.

A method for training one or more models configured to predict hormone receptor status comprises accessing a first set of H&E stain images from a first set of tissue samples having a positive hormone receptor status and a second set of H&E stain images from a second set of tissue samples having a negative hormone receptor status; partitioning each H&E stain image into a plurality of image tiles; for each H&E stain image, sampling a subset of image tiles from the plurality of image tiles; initializing a tile featurization model configured to generate a feature vector for an image tile, an attention model configured to generate an aggregate feature vector for a H&E stain image by aggregating feature vectors for a sampled subset of image tiles from the H&E stain image, and a prediction model configured to generate a prediction of hormone receptor status according to an aggregate feature vector; and training the tile featurization model, the attention model, and the prediction model synchronously with the first set of H&E stain images and the second set of H&E stain images. In additional embodiments, a non-transitory computer-readable storage medium stores instructions for performing the methods described herein. In additional embodiments, a system configured to perform the methods described herein comprises a processor and the non-transitory computer-readable storage medium.

BRIEF DESCRIPTION OF THE DRAWINGS

FIG. 3 illustrates a flowchart for training one or more models for predicting hormone receptor status from a H&E stain image, in accordance with one or more embodiments.

FIG. 5 illustrates graphs demonstrating example ERS predictive ability of the analytics system, in accordance with one or more embodiments.

Figure 1A:
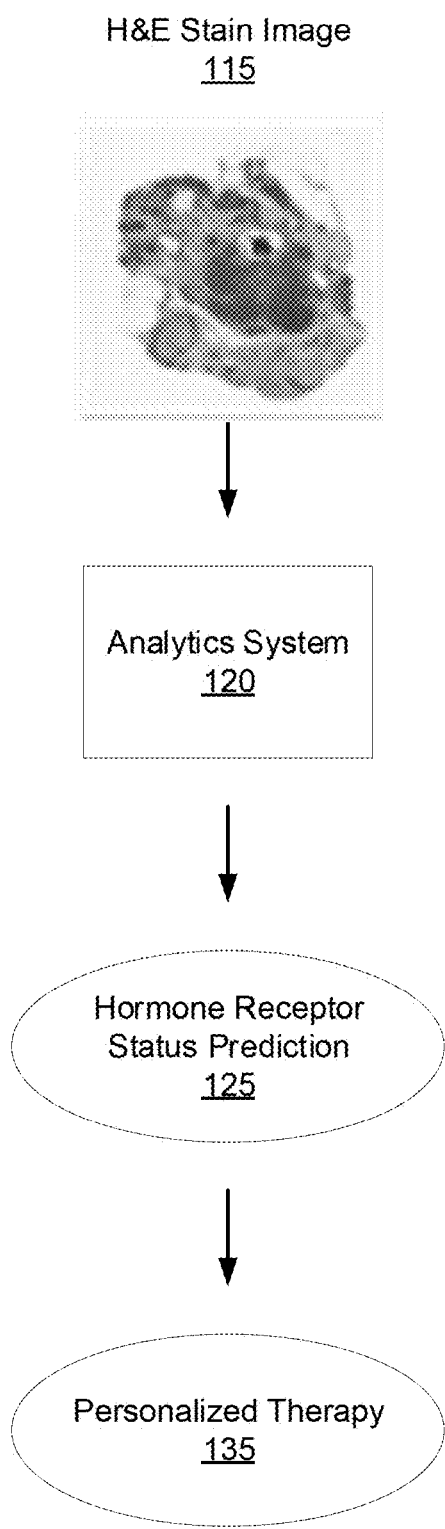
FIG. 1A illustrates a general flowchart for personalizing therapy by predicting hormone receptor status from a H&E stain image, in accordance with one or more embodiments.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

Overview

More than 1.7 million women across the world are diagnosed with breast cancer every year, resulting in 0.5 million annual deaths. A large majority of invasive breast cancers are hormone receptor-positive—the tumor cells grow in the presence of estrogen (ER) and/or progesterone (PR). Patients with hormone-receptor positive tumors often clinically benefit from receiving hormonal therapies, which target the estrogen signaling pathway. The US National Comprehensive Cancer Network guidelines mandate that hormone receptor status, including estrogen receptor status, be determined for every new breast cancer patient, as this is critical in clinical decision making.

In one diagnostic workflow, a patient's sample is thinly sectioned onto microscope slides for staining by a clinical technician followed by visual diagnosis by a pathologist. For breast cancer, ERS is also assayed using IHC staining with an antibody targeting the estrogen receptor. ERS is important as both a prognostic marker and predictive of endocrine therapy response. IHC staining and analysis has several limitations. First, IHC staining is expensive and time-consuming. The test output is expressed in terms of color: stain intensity, or percentage of cells that achieve a detectable stain intensity, or presence/absence of a stain; all of which are determined by a trained pathologist. There can also be significant variation in tissue sample quality due to differences in tissue handling and fixation by a technician, antibody sources and clones, and more generally a technician's skill level. Finally, the pathologists' decision-making process is inherently subjective and can result in human errors. These factors lead to discordance in ERS determination, placing patients at risk for suboptimal treatment.

A methodology described further herein predicts ERS from a H&E-stained whole slide image. The morphology shown in a H&E stained image is a reflection of the biology; in this case, the dependence on hormonal signaling and the arrangement of the cells may differ depending on the biology. Predicting ERS with H&E stain images has several advantages. For one, performing H&E stains is significantly cheaper than performing IHC stains. Moreover, H&E stain images exhibit less variability across imaging centers and are ubiquitously used in histopathology workflows globally. Predicting ERS with H&E stain images can thus reduce errors in tailoring breast cancer treatment—which generally improves treatment outcomes—and importantly can reduce time in formulating treatment decisions. Moreover, this methodology can be expanded to identify discriminative morphological features for molecular markers and has the potential to provide biological insights into how hormones drive tumor growth. Additional detail on the methodology and example results are provided in Appendix A, filed herewith.

FIG. 1A illustrates a general flowchart for personalizing therapy by predicting hormone receptor status from a H&E stain image 115, in accordance with one or more embodiments. An analytics system 120 is configured to receive the H&E stain image 115 from a biopsied tissue sample for an individual. The analytics system 120 generates an ERS prediction 125 according to the H&E stain image 115, the process of which will be further described below in FIGS. 2-4. The ERS prediction 125 can be used by a physician or other healthcare provider to formulate a personalized therapy 135 treatment plan for the individual. Note, the methodology described herein may be more generally applied to predict other hormone receptor statuses from a H&E stain image.

In one or more embodiments, the analytics system 120 implements machine instance learning (MIL). MTh algorithms, in general, learn from a training set of labeled bags of unlabeled instances. A positively labeled bag contains at least one positive instance, while a negatively labeled bag contains only negative instances. A trained MIL algorithm is able to predict a positive or negative label for a test bag. In the case of predicting ERS, a positively labeled ERS training H&E stain image has at least one image tile of a partitioned H&E stain image that is considered a positive instance, contributing to the positive label.

Analytics System Environment

Figure 1B:
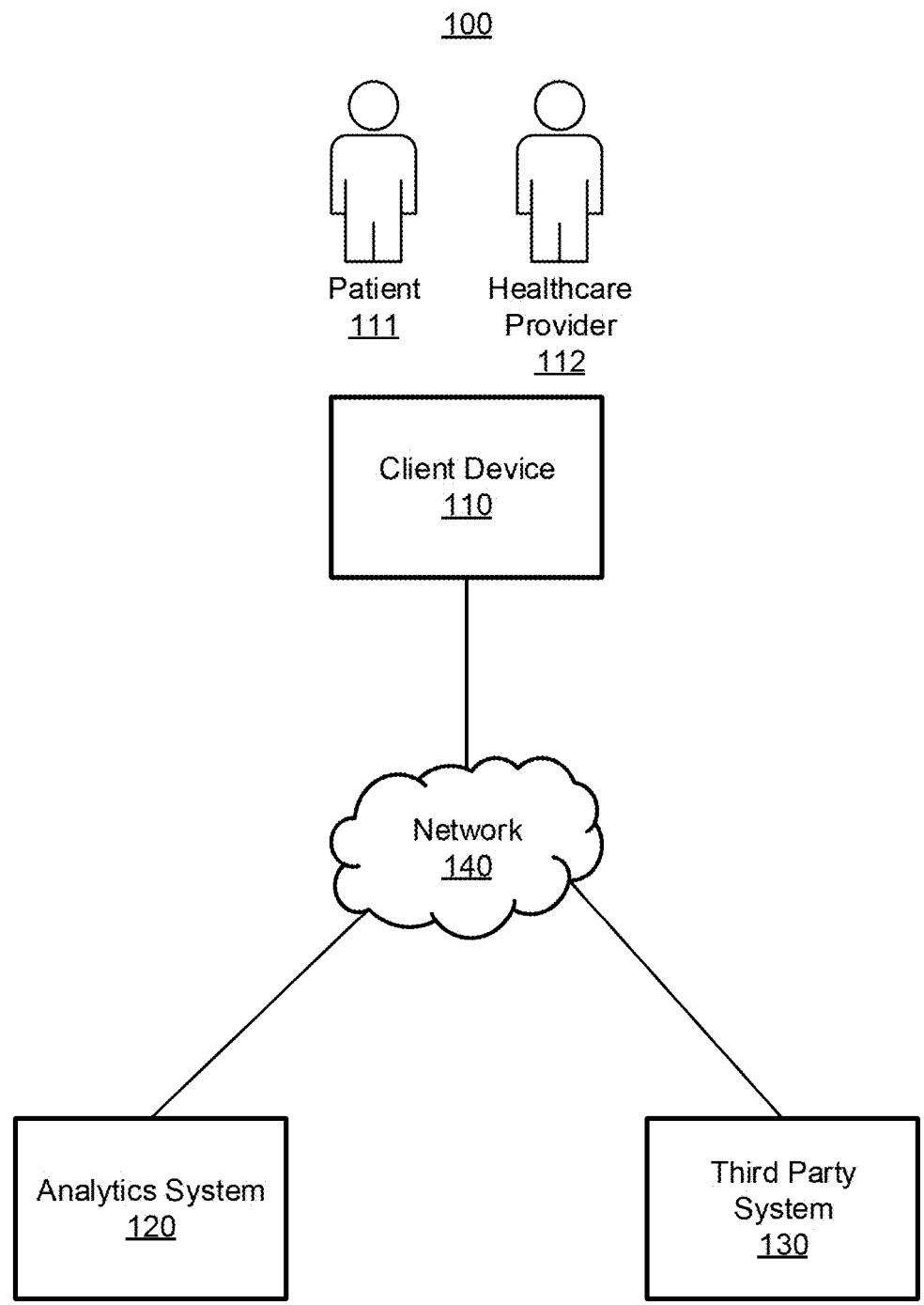
FIG. 1B illustrates an environment of an analytics system for predicting hormone receptor status, in accordance with one or more embodiments.

FIG. 1B illustrates an environment 100 of an analytics system 120 for predicting hormone receptor status, in accordance with one or more embodiments. In the environment 100, there are client device 110, the analytics system 120, and a third party system 130 in communication over a network 140. In other embodiments, the environment 100 includes additional or fewer components than those listed herein. For example, there may be any number of client devices 110 or any number of third party systems 130 in network with the analytics system 120.

A client device 110 is a computing system (such as a mobile phone, a computer, and the like) that interacts with the analytics system 120. The client device 110 may be configured to wirelessly communicate with the analytics system 120 via the network 140. For purposes of explanation and clarity it is useful to identify at least two different types of users. A patient 111 is a user seeking medical services.

Another type of user is a healthcare provider 112 who provides medical services to the patient 111. According to this present disclosure, the patient 111 utilizes a medical facility where a healthcare provider 112 performs a biopsy to obtain a tissue sample. The healthcare provider 112 (or another medical professional) performs a H&E stain on the tissue sample with a haematoxylin stain and an eosin stain. The healthcare provider 112 further captures a H&E stain image, e.g., via a microscope outfitted with a camera. The H&E stain image for the patient 111 is provided to the analytics system 120 by the client device 110. Furthermore, a prediction of a hormone receptor status, made by the analytics system 120 based on the patient's H&E stain image, is provided back to the client device 110. In some embodiments, the healthcare provider 112 may determine a diagnosis of a medical condition according to the hormone receptor status prediction from the analytics system 120. In other embodiments, the healthcare provider 112 may determine a personalized therapy according to the hormone receptor status prediction. For example, having predicted to have a positive ERS for a patient 111, the healthcare provider 112 can recommend hormonal therapies, either as a primary course of therapy or in combination with other therapies. Alternatively, if the patient 111 is predicted to have a negative ERS, the healthcare provider 112 may recommend other forms of therapy excluding hormonal therapy, e.g., surgery, chemotherapy, biological therapy, radiation therapy, or some combination thereof.

The analytics system 120 is a computing system (such as a server, a distributed network system, and the like) that predicts a hormone receptor status (e.g., ERS) according to a test H&E stain image of a biopsied tissue sample. The analytics system 120 trains one or more models used in predicting hormone receptor status from a test H&E stain image. The analytics system 120 trains the models with training H&E stain images labeled with a hormone receptor status, for instance as determined by a pathologist. The training H&E stain images may be obtained from the third party system 130. The analytics system 120 provides predictions of hormone receptor status for test H&E stain images to client devices 110 that provided the test H&E stain images. The analytics system 120 will be further described in FIG. 2.

The third party system 130 provides training H&E stain images to the analytics system 120. The third party system 130 collects biological data on various cancer types, the biological data including H&E stain images for various individuals with ERS labels. Other biological data may include, for example, qualitative analyses by trained medical professionals (e.g., annotations on H&E stain images), other hormone receptor status labels, sequencing data, protein expression data, metabolism data, etc. In one or more examples, a first third party system 130 stores data obtained by The Cancer Genome Atlas (TCGA) program and a second third party system 130 stores data obtained by the Australian Breast Cancer Tissue Bank (ABCTB).

The network 140 represents the various wired and wireless communication pathways between the client 110 devices, the sensor 120, the application server 130, and the database server 140. Network 140 uses standard Internet communications technologies and/or protocols. Thus, the network 140 can include links using technologies such as Ethernet, IEEE 802.11, integrated services digital network (ISDN), asynchronous transfer mode (ATM), etc. Similarly, the networking protocols used on the network 140 can include the transmission control protocol/Internet protocol (TCP/IP), the hypertext transport protocol (HTTP), the simple mail transfer protocol (SMTP), the file transfer protocol (FTP), etc. The data exchanged over the network 140 can be represented using technologies and/or formats including the hypertext markup language (HTML), the extensible markup language (XML), JavaScript Object Notation (JSON), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

Analytics System Architecture

Figure 2:
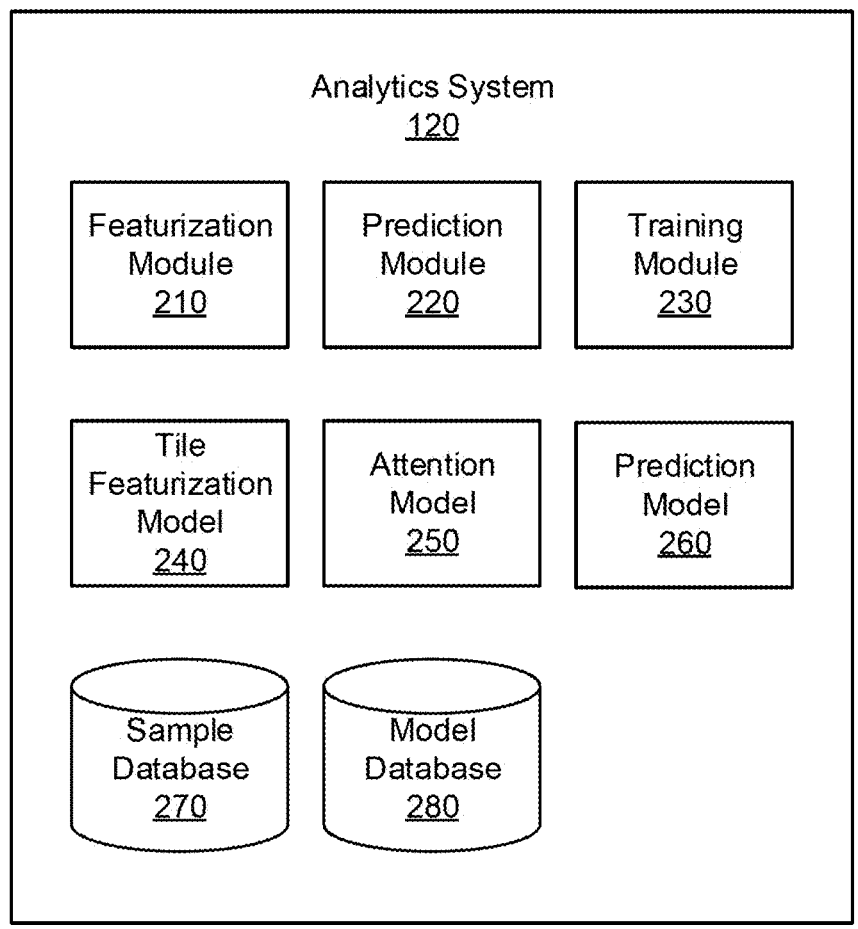
FIG. 2 illustrates an architecture of the analytics system for predicting hormone receptor status, in accordance with one or more embodiments.

FIG. 2 illustrates an architecture 200 of the analytics system 120 for predicting hormone receptor status, in accordance with one or more embodiments. The analytics system 120 predicts a hormone receptor status (e.g., ERS) for a test H&E stain image from a biopsied tissue sample. The analytics system 120 may further train one or more models for use in the prediction process. The analytics system 120 includes at least a featurization module 210, a prediction module 220, a training module 230, a tile featurization model 240, an attention model 250, a prediction model 260, a sample database 270, and a model database 280. The analytics system 120 may comprise additional or fewer components than those listed herein. In other embodiments, the various operations performed by the components may be variably distributed than as described herein this present disclosure.

The featurization module 210 partitions the H&E stain image into a plurality of image tiles (also referred to as "tiles" more generally). The tiles may be sized, e.g., 256 pixels by 256 pixels. The tiles may also be partitioned such that the tiles are non-overlapping. The featurization module 210 filters the tiles to obtain an initial set of tiles relating particularly to the stained biopsied tissue. In one implementation, the featurization module 210 uses Otsu thresholding that decides whether each image tile pertains to a foreground or a background, e.g., wherein the foreground relates to the stained biopsied tissue and the background relates to the slide on which the biopsied tissue is placed. In Otsu thresholding, the featurization module 210 searches through all available pixel intensities for the optimal threshold pixel intensity that minimizes intra-class variance (or equivalently, maximizing inter-class variance)—weighted sum of variance in the foreground and variance in the background. The image tiles in the foreground (relating to the stained biopsied tissue and not the slide) are retained in an initial set of tiles for the H&E stain image.

The featurization module 210 generates an aggregate feature vector for a H&E stain image for use in predicting a hormone receptor status from the initial set of image tiles. The featurization module 210 samples a subset of tiles from the initial set of tiles (the subset of tiles may also be referred to as a bag of tiles or, simply, a "bag"). For each tile in the sampled set, the featurization module 210 applies the tile featurization model 240 to the tile to generate a tile feature vector. The tile feature vector is a vector comprising a plurality of features extracted from the pixels in the image tile. In other embodiments, the featurization module 210 applies the tile featurization model 240 to all tiles in the sampled subset to generate a feature matrix. The featurization module 210 generates the aggregate feature vector for the H&E stain image by applying the attention model 250 to the tile feature vectors of the sampled subset. The attention model 240 combines the tile feature vectors by calculating a weighted sum of the tile feature vectors or the entries within the tile feature vectors to produce the aggregate feature vector. In embodiments implementing a MIL algorithm, the attention model 240 determines an attention weight to apply each tile feature vector or each tile feature vector entry based on the tile feature vector. The attention model 240 sums the tile feature vectors according to the attention weights to generate the aggregate feature vector. In this embodiment, the aggregate feature vector for the H&E stain image is of the same dimensionality as each tile feature vector. The attention weights are advantageous in increasing attention of image tiles that are more discriminatory in predicting the hormone receptor status. As noted above, a positive bag has at least one positive instance, such that the attention weights aim to identify and increase the influence of potential positive instances in a test H&E stain image.

The prediction module 220 generates a prediction of hormone receptor status according to the aggregate feature vector for a H&E stain image. The prediction module 220 applies the prediction model 260 to the aggregate feature vector to generate a hormone receptor status prediction. The hormone receptor status prediction may be binary (positive or negative) or may be a likelihood that the hormone receptor status is positive or negative, e.g., 90% likelihood of being positive. The hormone receptor status prediction may be provided to a client device 110, e.g., associated with a healthcare provider 112 for use by the healthcare provider 112 in determining a personalized treatment therapy.

In one or more embodiments, the analytics system 120 creates multiple bags from a test H&E stain image. The featurization module 210 partitions the test H&E stain image, and then creates multiple bags of randomly sampled tiles (e.g., having filtered for tiles relating to stained biopsied tissue). The featurization module 210 generates an aggregate feature vector for each bag, and the prediction model 220 generates a prediction for each bag. The overall prediction of hormone receptor status for the test H&E stain image may be cumulative of the predictions of the multiple bags.

The training module 230 trains the featurization model 240, the attention model 250, the prediction model 260, or any combination thereof. The training module 230 accesses training H&E stain images with labeled hormone receptor status (positive or negative) stored in the sample database 270. The training H&E stain images may be obtained by the analytics system 120 from one or more third party systems 130 and stored in the sample database 270. The training module 230 partitions each training H&E stain image into a plurality of image tiles, according to similar principles described above for the featurization module 210. The training module 230 creates one or more training bags of tiles as randomly sampled subsets of image tiles from a training H&E stain image. Each training bag is assigned the label from the training H&E stain image from which the training bag was created. The training module 230 may synchronously train the featurization model 240, the attention model 250, and the prediction model 260 through propagating the training bags through the models and adjusting model parameters of the models to minimize error between the assigned label for each bag and a predicted label output by the models. Training of the models may occur with batches of training bags (with cross-validation from one batch to another), wherein the models are trained over a plurality of epochs to sufficiently learn the training bags in a batch. In other embodiments, the training module 230 may train each model individually. The training module 230 may accomplish the training phase with batches of training bags and cross validate across batches of training. When sufficiently trained, the featurization model 240, the attention model 250, and the prediction model 260 may be used by the featurization module 210 and the prediction module 220 for predicting a hormone receptor status for a test H&E stain image.

In one or more embodiments, one or more of the models (the featurization model 240, the attention model 250, and the prediction model 260) is a neural network. Each neural network has a plurality of layers including at least an input layer with an input dimensionality and an output layer with an output dimensionality. The featurization model 240 has at least an input layer configured to receive an image tile in a sampled subset (or bag) and an output layer configured to output a tile feature vector based on the image tile. The attention model 240 has an input layer configured to receive the tile feature vectors for a sampled subset (or bag) and an output layer configured to output an aggregate feature vector for the sampled subset. An internal layer of the attention model 240 may determine the attention weights for each of the tile feature vectors in the sampled subset. The prediction model 260 has at least an input layer configured to receive the aggregate feature vector of a sampled subset and an output layer configured to output a hormone receptor status prediction label. During training of the models, the training module 230 propagates training bags through the models to predict a hormone receptor status and backpropagates through the models (adjusting parameters of each model) to minimize error between the prediction and the correct label.

In one example, the input layer for the featurization model 240 receives pixel intensities for a 256 pixel by 256 pixel image tile; the output layer outputs a vector of 512 features. Continuing with this example, the input layer for the attention model 240 receives fifty tile feature vectors, each of dimensionality 512; the output layer outputs an aggregate feature vector of dimensionality 512. Finally, the input layer of the prediction model 260 receives the aggregate feature vector of dimensionality 512; the output layer outputs a prediction of positive or negative for the hormone receptor status.

In other embodiments, other machine learning (ML) algorithms may be implemented for each of the models. Other ML algorithms that may be used include, but are not limited to, regression algorithms, classifier algorithms, decision tree algorithms, mixture models, a convolutional neural network, or another supervised learning approach.

In one or more embodiments, the analytics system 120 uses a single aggregate model that is configured to perform the operations of the tile featurization model 240, the attention model 250, and the prediction model 260. The trained aggregate model is configured to receive the bag of tiles for a H&E stain image and to output a prediction of hormone receptor status. The training module 230 trains the aggregate model in a similar fashion in embodiments with training the tile featurization model 240, the attention model 250, and the prediction model 260.

In one or more embodiments, the training module 230 implements cutout regularization on the training H&E stain images. In cutout regularization, the training module 230 excludes portions of a training H&E stain image in the training phase. Training bags are then sampled from the remaining portion of the training H&E stain image. The training module 230 may have various cutout regularization parameters that dictate the cutout regularization. For example, there may be some probability that the training module 230 applies cutout regularization to a training H&E stain image or a frequency at which the cutout regularization is applied, e.g., every $50^{th}$ training H&E stain image. Cutout regularization is advantageous in exhaustively learning discriminatory features in the H&E stain images that might otherwise be overlooked in the presence of stronger features.

In one or more embodiments, the training module 230 implements mean pixel regularization to training bags. In mean pixel regularization, the training module 230 overwrites a tile in a bag by replacing all pixel values to a mean pixel intensity of the training H&E stain images. As with the cutout regularization, the probability (or frequency) of performing mean pixel regularization to a tile in a bag may be an adjustable parameter. Mean pixel regularization is advantageous in preventing overfitting during the training phase of the models. Other regularizations may also be implemented to one or more tiles to increase variance in the training. As one or more examples, a rotational regularization rotates a tile, a mirror regularization mirrors a tile (left-right or up-down), and a color jittering regularization jitters one or more colors of a tile.

In one or more embodiments, the training module 230 implements hard negative mining during the training phase. In one embodiment of hard negative mining, the training module 230 identifies incorrectly predicted training bags in an epoch of training and retains such training bags in a subsequent epoch of training. In another embodiment, the training module 230 retains the incorrectly predicted training bags upon completion of training of a batch for use in a subsequent batch. Hard negative mining may help ensure sufficient learning with all training bags in a batch.

The sample database 270 stores H&E stain images from stained biopsied tissue samples. The sample database 270 stores training H&E stain images obtained from one or more third party systems 130 and test H&E stain images received from client devices 110. Each of the training H&E stain images may include one or more labels for various hormone receptor statuses. According to one embodiment, each training H&E stain image hast at least a label, positive or negative, for ERS.

The model database 280 stores the models used by the analytics system 120. The models include the featurization model 240, the attention model 250, and the prediction model 260. In one or more embodiments, the model database 280 stores sets of models trained to predict different hormone receptor statuses. For example, a first set of models is trained to predict ERS with a second set of models trained to predict another hormone receptor status. As another example, the featurization model 240 may be generally used for predicting different hormone receptor statuses while each hormone receptor status may have a uniquely trained attention model 250 and prediction model 260. In storing models, the model database 280 stores all the model parameters for each model, e.g., trained by the training module 230.

Hormone Receptor Status Prediction Flowcharts

FIG. 3 illustrates a flowchart of a method 300 for training one or more models for predicting hormone receptor status from a H&E stain image, in accordance with one or more embodiments. The method 300 can be performed by the analytics system 120 (and more specifically by the training module 230 of the analytics system 120). In other embodiments, there may be additional or fewer operations than those listed herein, while maintaining the core principles of the training phase.

The analytics system 120 accesses 310 a first set of H&E stain images of tissue samples having positive hormone receptor status and a second set of H&E stain images of tissue samples having negative hormone receptor status. The first set and the second set may be obtained from third party systems.

For each H&E stain image, the analytics system 120 partitions 320 the H&E stain image into a plurality of image tiles. The plurality of image tiles may be non-overlapping. Further, the analytics system 120 may filter out image tiles not pertaining to the stained biopsied tissue, e.g., with Otsu thresholding. At this step, the analytics system 120 may additionally implement cutout regularization to exclude portions of one or more H&E stain images from the first set and the second set.

For each H&E stain image, the analytic system 120 samples 330 a subset of image tiles from the image tiles of the H&E stain image (e.g., defined as a training bag). The sampling may be random. Moreover, multiple training bags may be derived from each H&E stain image used for training. At this step, the analytics system 120 may additionally implement mean pixel regularization to overwrite one or more tiles in one or more training bags with a mean pixel intensity over the first set and the second set.

The analytics system 120 trains 340 a featurization model configured to generate a tile feature vector for an image tile. The analytics system 120 trains 350 an attention model configured to generate an aggregate feature vector for a H&E stain image by aggregating the tile feature vectors of the image tiles in the sampled subset. The analytics system 120 trains 360 a prediction model configured to predict hormone receptor status using the aggregate feature vector from a H&E stain image. In the embodiment of FIG. 3, the analytic system 120 trains the featurization model, the attention model, and the prediction model with the training bags derived from the first set and the second set.

In one or more embodiments, the analytics system 120 trains the featurization model, the attention model, and the prediction model synchronously. Batches of training bags may be collated and used for iterative batch training of the models. Hard negative mining may be implemented during the training phase. The trained models are useful for predicting a hormone receptor status for a test H&E stain image of unknown hormone receptor status.

Figure 4:
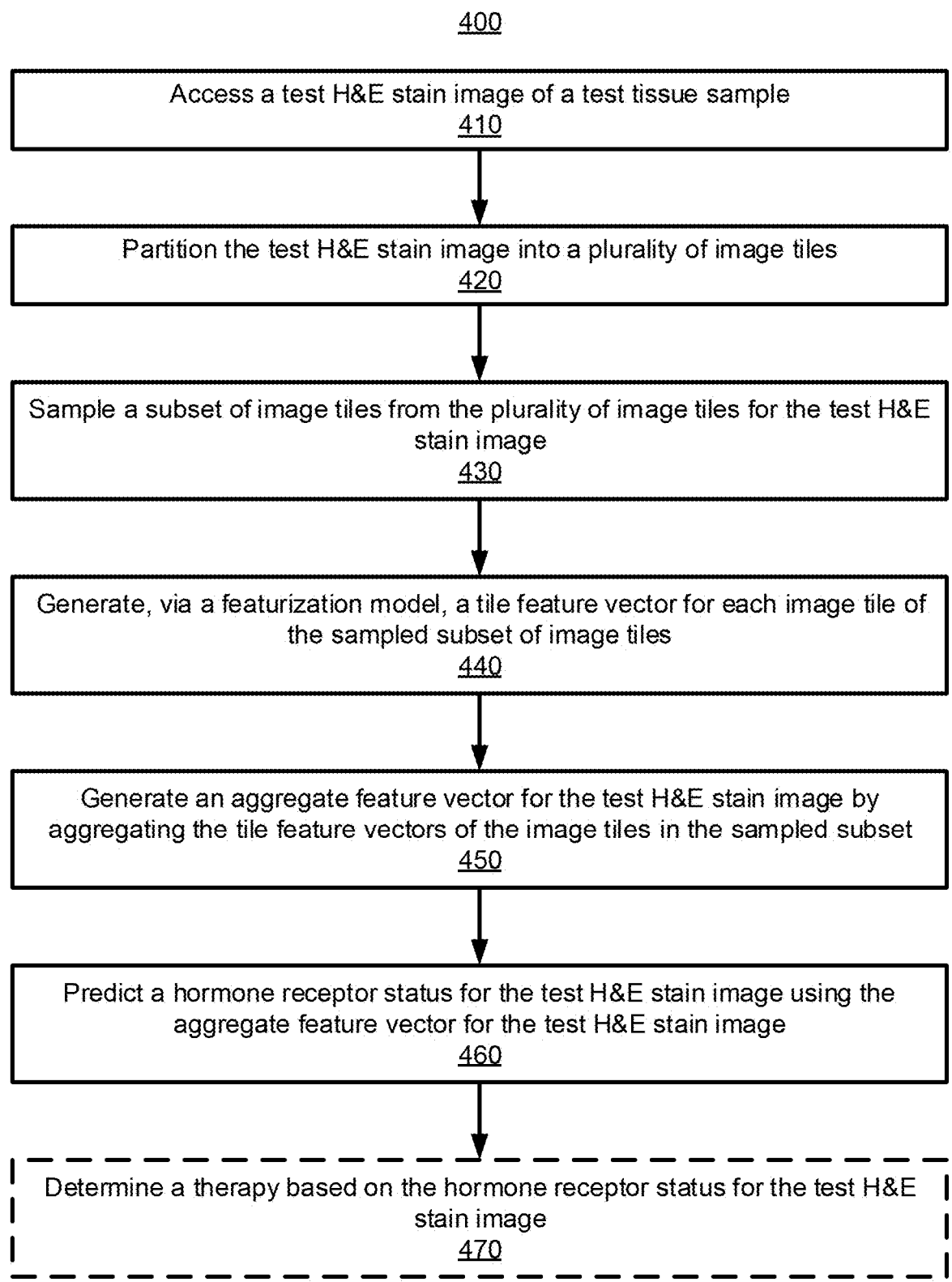
FIG. 4 illustrates a flowchart for predicting hormone receptor status from a test H&E stain image, in accordance with one or more embodiments.

FIG. 4 illustrates a flowchart of a method 400 for predicting hormone receptor status from a test H&E stain image, in accordance with one or more embodiments. The method 400 can be performed by the analytics system 120 (and more specifically by the featurization module 210 and the prediction module 220 of the analytics system 120). In other embodiments, there may be additional or fewer operations than those listed herein, while maintaining the core principles of the prediction phase.

The analytics system 120 access 410 a test H&E stain image of a test tissue sample. The test H&E stain image may be obtained from a client device 110, for instance associated with a medical professional that biopsies, stains, and images the test tissue sample.

The analytics system 120 partitions 420 the test H&E stain image into a plurality of image tiles. The plurality of image tiles may be non-overlapping. Further, the analytics system 120 may filter out image tiles not pertaining to the stained biopsied tissue, e.g., using Otsu thresholding.

The analytics system 120 samples 430 a subset of image tiles from the plurality of image tiles for the test H&E stain image. The analytics system 120 may randomly sample (e.g., 50 tiles in a bag) the image tiles. In one or more embodiments, the analytics system 120 creates multiple bags from the test H&E stain image for use in prediction—multi-bag prediction. Each of the bags may be checked to ensure uniqueness.

The analytics system 120 generates 440, via a featurization model, a tile feature vector for each image tile of the sampled subset of image tiles. The featurization model is trained, e.g., according to the flowchart 300, and is configured to receive an image tile and to output a tile feature vector.

The analytics system 120 generates 450 an aggregate feature vector for the test H&E stain image by aggregating the tile feature vectors of the image tiles in the sampled subset. The analytics system 120 may apply an attention model (e.g., trained according to the flowchart 300) to the tile feature vectors in the sampled subset. The attention model is trained to determine an attention weight to each tile feature vector to increase attention of high discriminatory tile feature vectors when aggregating to generate the aggregate feature vector. The attention model may also output the attention weight for each of the image tiles. In embodiments in multi-bag prediction, the analytics system 120 separately generates an aggregate feature vector for each bag derived from the test H&E stain image.

The analytics system 120 predicts 460 a hormone receptor status for the test H&E stain image using the aggregate feature vector for the test H&E stain image. The analytic system 120 may apply a prediction model (e.g., trained according to the flowchart 300) to the aggregate feature vector in order to generate a prediction of the hormone receptor status. The prediction may be binary, positive or negative. Alternatively or in addition to the binary result, the prediction may be a percent likelihood of positive or negative. In multi-bag prediction embodiments, the analytics system 120 generates a prediction for each bag and accumulates the predictions over the multiple bags.

The analytics system 120 may determine 470 a therapy based on the hormone receptor status for the test H&E stain image. The therapy may be tailored according to the result, positive or negative. As mentioned above, a positive hormone receptor status may indicate a positive reception to hormonal therapies in treating a cancer type. On the other hand, a negative hormone receptor status may indicate a lack of response to hormonal therapies thus leading to suggestion of therapies alternative to hormonal.

Example Data

Figure 6:
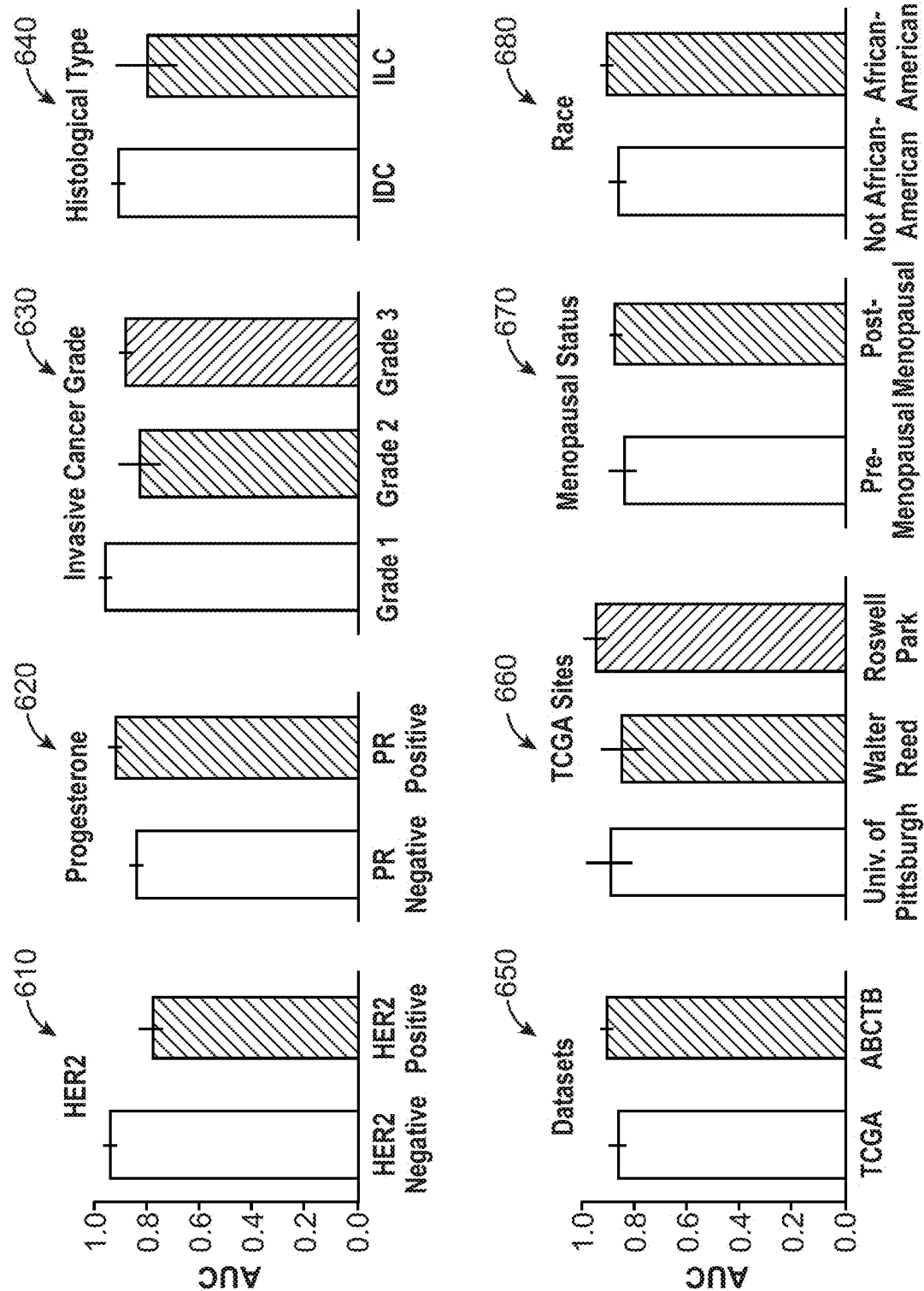
FIG. 6 illustrates graphs demonstrating example ERS predictive ability of the analytics system screened by additional factors, in accordance with one or more embodiments.

In the embodiments of FIGS. 5 and 6, the analytics system 120 trained the models (referred to herein as "AttentionNet") according to the flowchart 300 with implementations details as described below. The analytics system 120 trained the models using H&E images obtained from the Australian Breast Cancer Tissue Bank (ABCTB) dataset which contains 2,535 H&E images from 2,535 patients and The Cancer Genomic Atlas (TCGA) dataset which contains 1,014 H&E images from 939 patients. To initialize the featurization model 240, the analytics system initialized with ImageNet32-pretrained weights and the fully-connected layers are randomly initialized using He initialization31. A first part of the attention model 250 contains a linear layer which reduces each tile feature vector to 128 dimensions and applies an element-wise hyperbolic tangent nonlinearity, which scales the features to include values between −1 and 1 and facilitates learning of similarities and contrasts between tiles. The output of this linear layer followed by tangent hyperbolic function is multiplied by another linear layer and a softmax function which computes a scalar "attention weight" between 0-1 for a particular tile. An inner product of the attention vector the feature matrix comprising the tile feature vectors obtains the aggregate feature vector. The aggregate feature vector is fed to the prediction model 260 followed by a sigmoid function, which outputs a probability between 0 and 1 for a bag of tiles.

FIG. 5 illustrates graphs demonstrating example ERS predictive ability of the analytics system 120, in accordance with one or more embodiments.

Graphs 510 and 520 shows receiver operating characteristic (ROC) curves that plot sensitivity (true positive rate) to specificity (false positive rate) over a domain of thresholds used to predict between positive and negative ERS. Graph 510 shows a ROC curve for the cross-validation of the trained models demonstrating an area under the curve (AUC) metric of 0.90 for the binary classification with a 95% confidence interval between 0.884 and 0.913, wherein an AUC metric of 1 is a perfect binary classification and a AUC metric of 0.5 is as good as random binary classification. Graph 520 shows a ROC curve for a test set of H&E stain images demonstrating an AUC metric of 0.92 for binary classification with a 95% confidence interval between 0.892 and 0.946.

Graph 530 compares AttentionNet's performance with other competitive MIL algorithms Meanpool and Maxpool. The performance of the competitive algorithms is inferior to AttentionNet on the test set. Meanpool obtains an AUC metric of 0.827 (95% CI: 0.786, 0.866) and Maxpool obtains an AUC of 0.880 (95% CI: 0.846, 0.912). A baseline logistic regression model using pathologist-provided histological type and tumor grade was also compared demonstrating an AUC metric of 0.809 (95% CI: 0.766, 0.848), significantly lower than AttentionNet.

FIG. 6 illustrates graphs demonstrating example ERS predictive ability of the analytics system 120 screened by additional factors, in accordance with one or more embodiments.

Graph 610 compares the ERS predictive ability of AttentionNet in light of human epidermal growth factor receptor 2 (HER2). HER2 overexpression is a dominant transformation mechanism in tumors. AttentionNet performs significantly better on HER2 negative samples (AUC=0.927, 95% CI: 0.912, 0.943) as compared to HER2 positive samples (AUC=0.768, 95% CI: 0.719, 0.813).

Graph 620 compares the ERS predictive ability of AttentionNet in light of progesterone (PR). AttentionNet performs better on PR positive samples (AUC=0.906, 95% CI: 0.869, 0.940) as compared to PR negative samples (AUC=0.827, 95% CI: 0.795, 0.855), which is reflective of the high correlation between ER and PR statuses.

Graph 630 compares the ERS predictive ability of AttentionNet in light of varying tumor grade for breast cancer (1, 2, or 3), AUC metric of 0.949 for grade 1 (95% CI: 0.925, 0.973), AUC metric of 0.810 for grade 2 (95% CI: 0.716, 0.888), and AUC metric of 0.865 for grade 3 (95% CI: 0.840, 0.887).

Graph 640 compares the ERS predictive ability of AttentionNet in light of whether the tumor was ductal (IDC) or lobular (ILC) in origin. There was no statistical difference between the IDC or ILC.

Graph 650 compares the ERS predictive ability of AttentionNet in light of source of H&E stain images from TCGA or ABCTB. There was no statistical difference. On the cross-validation of the training set, the AUC metric on TCGA is 0.861 (95% CI: 0.828, 0.893); the AUC metric on ABCTB is 0.905 (95% CI: 0.889, 0.921).

Graph 660 compares the ERS predictive ability of AttentionNet in light of sites of H&E stain images collected under TCGA. There was no statistical difference. Performance across 42 TCGA tissue source sites is similar and is not dependent on the proportion of training samples collected from a given site.

Graph 670 compares the ERS predictive ability of AttentionNet in light of menopausal status. AUC metric for post-menopausal women is 0.872 (95% CI: 0.832, 0.908). AUC metric for pre-menopausal women is 0.838 (95% CI: 0.779, 0.893). There was no statistical difference.

Graph 680 compares the ERS predictive ability of AttentionNet in light of race AUC metric for African-American patients is 0.859 (95% CI: 0.785, 0.921). AUC for the rest of the patients is 0.858 (95% CI: 0.817, 0.896). There was no statistical difference.

Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment, thereby providing a framework for various possibilities of described embodiments to function together.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for predicting hormone receptor status using machine learning comprising:
 accessing a test haematoxylin and eosin (H&E) stain image of a test tissue sample;
 partitioning the test H&E stain image into a plurality of non-overlapping image tiles;
 sampling a subset of non-overlapping image tiles from the plurality of non-overlapping image tiles of the test H&E stain image;
 generating a tile feature vector for one or more non-overlapping image tiles of the sampled subset of non-overlapping image tiles;
 generating an aggregate feature vector for the test H&E stain image by aggregating the tile feature vectors of the non-overlapping image tiles of the sampled subset; and
 predicting a hormone receptor status by applying a machine-learned prediction model to the aggregate feature vector for the test H&E stain image, wherein the machine-learned prediction model is trained using a first set of H&E stain images from a first set of tissue samples having a positive hormone receptor status and a second set of H&E stain images from a second set of tissue samples having a negative hormone receptor status.

2. The method of claim 1, wherein the hormone receptor status comprises an estrogen receptor status.

3. The method of claim 1, wherein the plurality of image tiles are non-overlapping.

4. The method of claim 1, further comprising filtering the plurality of non-overlapping image tiles to retain non-overlapping image tiles pertaining to the test tissue sample, wherein the sampled subset of non-overlapping image tiles is sampled from the non-overlapping image tiles pertaining to the test tissue sample.

5. The method of claim 1, wherein generating the tile feature vector for the one or more non-overlapping image tile comprises applying a tile featurization model to each non-overlapping image tile.

6. The method of claim 5, wherein generating the aggregate feature vector comprises applying an attention model to the tile feature vectors of the sampled subset of non-overlapping image tiles, wherein the attention model is configured to determine, for each tile feature vector of the sampled subset, an attention weight based on each tile feature vector and to sum products of each attention weight and the respective tile feature vector to produce the aggregate feature vector.

7. The method of claim 6, wherein the featurization model, the attention model, and the machine-learned prediction model are trained synchronously using the first set of H&E stain images from the first set of tissue samples having the positive hormone receptor status and the second set of H&E stain images from the second set of tissue samples having the negative hormone receptor status.

8. The method of claim 1, wherein the predicted hormone receptor status is one of:
 a positive status or a negative status; and
 a likelihood of a positive status or a likelihood of a negative status.

9. The method of claim 1, further comprising:
 sampling a second subset of non-overlapping image tiles from the plurality of non-overlapping image tiles of the test H&E stain image;
 generating a tile feature vector for one or more non-overlapping image tiles of the second sampled subset of non-overlapping image tiles;
 generating a second aggregate feature vector for the test H&E stain image by aggregating the tile feature vectors of the non-overlapping image tiles of the second sampled subset; and
 predicting a second hormone receptor status by applying the machine-learned prediction model to the second aggregate feature vector, wherein a cumulative prediction of the hormone receptor status combines the hormone receptor status and the second hormone receptor status.

10. A non-transitory computer-readable storage medium storing instructions that, when executed by a processor, cause the processor to perform operations comprising:
 accessing a test haematoxylin and eosin (H&E) stain image of a test tissue sample;
 partitioning the test H&E stain image into a plurality of non-overlapping image tiles;
 sampling a subset of non-overlapping image tiles from the plurality of non-overlapping image tiles for the test H&E stain image;
 generating a tile feature vector for one or more non-overlapping image tiles of the sampled subset of image tiles;
 generating an aggregate feature vector for the test H&E stain image by aggregating the tile feature vectors of the non-overlapping image tiles in the sampled subset; and
 predicting a hormone receptor status by applying a machine-learned prediction model to the aggregate feature vector for the test H&E stain image, wherein the machine-learned prediction model is trained using a first set of H&E stain images from a first set of tissue samples having a positive hormone receptor status and a second set of H&E stain images from a second set of tissue samples having a negative hormone receptor status.

11. The storage medium of claim 10, the operations further comprising filtering the plurality of non-overlapping image tiles to retain non-overlapping image tiles pertaining to the test tissue sample, wherein the sampled subset of non-overlapping image tiles is sampled from the non-overlapping image tiles pertaining to the test tissue sample.

12. The storage medium of claim 10,
 wherein generating the tile feature vector for one or more non-overlapping image tiles comprises applying a tile featurization model to each non-overlapping image tile,
 wherein generating the aggregate feature vector comprises applying an attention model to the tile feature vectors of the sampled subset of image tiles, wherein the attention model is configured to determine, for each tile feature vector of the sampled subset, an attention weight based on each tile feature vector and to sum products of each attention weight and the respective tile feature vector to produce the aggregate feature vector, and wherein the featurization model, the attention model, and the machine-learned prediction model are trained synchronously using the first set of H&E stain images from the first set of tissue samples having the positive hormone receptor status and the second set of H&E stain images from the second set of tissue samples having the negative hormone receptor status.

13. The storage medium of claim 10, the operations further comprising:
sampling a second subset of non-overlapping image tiles from the plurality of non-overlapping image tiles of the test H&E stain image;
generating a tile feature vector for one or more non-overlapping image tiles of the second sampled subset of non-overlapping image tiles;
generating a second aggregate feature vector for the test H&E stain image by aggregating the tile feature vectors of the non-overlapping image tiles of the second sampled subset; and
predicting a second hormone receptor status by applying the machine-learned prediction model to the second aggregate feature vector, wherein a cumulative prediction of the hormone receptor status combines the hormone receptor status and the second hormone receptor status.

14. A method for training one or more machine-learned models configured to predict hormone receptor status comprising:
accessing a first set of H&E stain images from a first set of tissue samples having a positive hormone receptor status and a second set of H&E stain images from a second set of tissue samples having a negative hormone receptor status;
partitioning each H&E stain image in the first set of H&E stain images and the second set of H&E stain images into a plurality of non-overlapping image tiles;
for each partitioned H&E stain image, sampling a subset of non-overlapping image tiles from the plurality of non-overlapping image tiles;
initializing a tile featurization model configured to generate a feature vector for a non-overlapping image tile, an attention model configured to generate an aggregate feature vector for a H&E stain image by aggregating feature vectors for a sampled subset of non-overlapping image tiles from the H&E stain image, and a prediction model configured to generate a prediction of hormone receptor status based on an aggregate feature vector; and
training the tile featurization model, the attention model, and the prediction model using the first set of H&E stain images and the second set of H&E stain images.

15. The method of claim 14, further comprising:
excluding a portion of one or more H&E stain images determined to be non-relevant to hormone receptor status, wherein the sampled subset of non-overlapping image tiles does not include non-overlapping image tiles from the excluded portions of H&E stain images.

16. The method of claim 14, further comprising:
overwriting a non-overlapping image tile in a sampled subset with a mean pixel intensity of the H&E stain image from which the non-overlapping image tile is partitioned.

17. The method of claim 14, wherein at least one of the tile featurization model, the attention model, and the prediction model is a neural network trained via backpropagation.

18. The method of claim 14, wherein training the tile featurization model, the attention model, and the prediction model occurs in batches of sampled subsets, wherein each batch of sampled subsets is trained over a plurality of epochs.

19. The method of claim 14, wherein training the prediction model further comprises:
in a first epoch, identifying one or more sampled subsets predicted incorrectly by the prediction model; and
including the one or more sampled subsets predicted incorrectly in a second epoch subsequent to the first epoch.

20. The method of claim 14, further comprising applying, to a sampled subset, one of:
a rotation regularization which rotates one or more non-overlapping image tiles;
a mirror regularization which mirror flips one or more non-overlapping image tiles; and
a color jittering regularization which jitters one or more colors of one or more non-overlapping image tiles.

* * * * *

UNITED STATES PATENT AND TRADEMARK OFFICE
CERTIFICATE OF CORRECTION

PATENT NO. : 11,508,481 B2
APPLICATION NO. : 16/895983
DATED : November 22, 2022
INVENTOR(S) : Naik et al.

It is certified that error appears in the above-identified patent and that said Letters Patent is hereby corrected as shown below:

On the Title Page

In Column 2, below "ABSTRACT", Line 17, delete "20 Claims," and insert -- 19 Claims, --, therefor.

In the Specification

In Column 1, Line 27, above "A method for predicting hormone receptor status using" insert
-- SUMMARY --. (section heading)

In the Claims

In Column 13, Claim 3, Lines 40-41, delete "3. The method of claim 1, wherein the plurality of image tiles are non-overlapping".

In Column 13, Claim 4, Line 42, delete "4. The" and insert -- 3. The --, therefor.

In Column 13, Claim 5, Line 48, delete "5. The" and insert -- 4. The --, therefor.

In Column 13, Claim 6, Line 52, delete "6. The method of claim 5," and insert -- 5. The method of claim 4, --, therefor.

In Column 13, Claim 7, Line 61, delete "7. The method of claim 6," and insert -- 6. The method of claim 5, --, therefor.

In Column 14, Claim 8, Line 1, delete "8. The" and insert -- 7. The --, therefor.

In Column 14, Claim 9, Line 6, delete "9. The" and insert -- 8. The --, therefor.

In Column 14, Claim 10, Line 23, delete "10. A" and insert -- 9. A --, therefor.

Signed and Sealed this
Sixteenth Day of May, 2023

Katherine Kelly Vidal
Director of the United States Patent and Trademark Office

CERTIFICATE OF CORRECTION (continued)
U.S. Pat. No. 11,508,481 B2

In Column 14, Claim 11, Line 49, delete "11. The storage medium of claim 10," and insert -- 10. The storage medium of claim 9, --, therefor.

In Column 14, Claim 12, Line 55, delete "12. The storage medium of claim 10," and insert -- 11. The storage medium of claim 9, --, therefor.

In Column 15, Claim 13, Line 8, delete "13. The storage medium of claim 10," and insert -- 12. The storage medium of claim 9, --, therefor.

In Column 15, Claim 14, Line 26, delete "14. A" and insert -- 13. A --, therefor.

In Column 16, Claim 15, Line 8, delete "15. The method of claim 14," and insert -- 14. The method of claim 13, --, therefor.

In Column 16, Claim 16, Line 15, delete "16. The method of claim 14," and insert -- 15. The method of claim 13, --, therefor.

In Column 16, Claim 17, Line 20, delete "17. The method of claim 14," and insert -- 16. The method of claim 13, --, therefor.

In Column 16, Claim 18, Line 24, delete "18. The method of claim 14," and insert -- 17. The method of claim 13, --, therefor.

In Column 16, Claim 19, Line 29, delete "19. The method of claim 14," and insert -- 18. The method of claim 13, --, therefor.

In Column 16, Claim 20, Line 36, delete "20. The method of claim 14," and insert -- 19. The method of claim 13, --, therefor.